(12) United States Patent
Leonardi et al.

(10) Patent No.: US 7,137,952 B2
(45) Date of Patent: Nov. 21, 2006

(54) INTRAOCULAR PRESSURE RECORDING SYSTEM

(75) Inventors: Matteo Leonardi, Lausanne (CH); Stefan Metz, Lausanne (CH); Daniel Bertrand, Geneva (CH); Peter Leuenberger, Conches (CH)

(73) Assignee: Ecole Polytechnique Federale de Lausanne-Service des Relations Industrielles, Lausanne (CH)

( * ) Notice: Subject to any disclaimer, the term of this patent is extended or adjusted under 35 U.S.C. 154(b) by 86 days.

(21) Appl. No.: 10/481,813

(22) PCT Filed: Jun. 29, 2001

(86) PCT No.: PCT/CH01/00407

§ 371 (c)(1),
(2), (4) Date: Jan. 29, 2004

(87) PCT Pub. No.: WO03/001991

PCT Pub. Date: Jan. 9, 2003

(65) Prior Publication Data

US 2004/0186366 A1    Sep. 23, 2004

(51) Int. Cl.
*A61B 3/16* (2006.01)
*A61B 5/00* (2006.01)
*A61B 5/103* (2006.01)

(52) U.S. Cl. .................. 600/398; 600/561; 600/587

(58) Field of Classification Search ........... 600/398, 600/399, 400, 402, 405, 406, 561, 587; 351/219
See application file for complete search history.

(56) References Cited

U.S. PATENT DOCUMENTS

| | | | |
|---|---|---|---|
| 3,958,560 A | 5/1976 | March | |
| 4,089,329 A | 5/1978 | Couvillon, Jr. et al. | |
| 4,305,399 A | 12/1981 | Beale | |
| 4,922,913 A | 5/1990 | Waters et al. | |
| 5,005,577 A | 4/1991 | Frenkel | |
| 5,179,953 A | 1/1993 | Kursar | |
| 5,217,015 A * | 6/1993 | Kaye et al. | 600/405 |
| 5,840,041 A * | 11/1998 | Petter et al. | 600/547 |
| 6,123,668 A * | 9/2000 | Abreu | 600/405 |
| 6,213,943 B1 | 4/2001 | Abreu | |
| 6,287,256 B1 | 9/2001 | Park et al. | |
| 6,405,069 B1 | 6/2002 | Oraevsky et al. | |

(Continued)

FOREIGN PATENT DOCUMENTS

EP    0 061 777    10/1982

(Continued)

OTHER PUBLICATIONS

Myron, et al, "A scleral buckle pressure gauge for continuous monitoring of intraocular pressure," International Ophthalmology 2, 3: 11-17 (1980).

(Continued)

*Primary Examiner*—Charles Marmor
(74) *Attorney, Agent, or Firm*—Nixon & Vanderhye P.C.

(57) ABSTRACT

A new noninvasive approach for intraocular pressure (IOP) measurement allowing continuous monitoring over prolonged periods, regardless of patient's position and activities. The key element of this measurement method is a soft contact lens (1) including at least one strain gage (2) longitudinally arranged around the center of the contact lens and capable of measuring precisely spherical deformations of the eyeball induced by the changes in IOP. This information is transmitted with wires or (preferably) wirelessly in real time to an external recording system (14). The system is placed in the same way as a normal corrective contact lens, no anesthesia is required and patient vision remains almost completely unimpaired.

23 Claims, 5 Drawing Sheets

U.S. PATENT DOCUMENTS

| | | | |
|---|---|---|---|
| 6,447,449 | B1 | 9/2002 | Fleischman et al. |
| 6,517,483 | B1 * | 2/2003 | Park et al. ................. 600/398 |
| 6,579,235 | B1 * | 6/2003 | Abita et al. ................. 600/398 |
| 6,746,400 | B1 | 6/2004 | Rathjen |
| 2002/0159031 | A1 | 10/2002 | Kanngiesser |
| 2003/0225318 | A1 | 12/2003 | Montegrande et al. |
| 2004/0116794 | A1 | 6/2004 | Fink et al. |

FOREIGN PATENT DOCUMENTS

| | | |
|---|---|---|
| EP | 0926979 | 3/1998 |
| GB | 2374925 | 10/2002 |
| WO | WO9809564 A1 | 3/1998 |
| WO | WO 9901063 | 1/1999 |
| WO | WO 0045693 | 8/2000 |
| WO | WO03088867 | 10/2003 |
| WO | WO 2004064629 | 8/2004 |

OTHER PUBLICATIONS

"Distensibility measurements of the rabbit eye," Tittel & Richards, Investigative Ophthalmology, 1971, vol. 10, No. 10, 800-809.

Schnakenberg et al, "Initial investigations on systems for measuring intraocular pressure", Sensors and Actuators A. Elsevier Sequoia S.A., Lausanne, CH, vol. 85,k No. 1-3, Aug. 25, 2000, pp. 287-291.

Greene et al, "Intraocular pressure measurement with instrumented contact lenses", Investigative Ophthalmology, vol. 13, No. 4, Apr. 1974, pp. 299-302.

* cited by examiner

INTRAOCULAR PRESSURE RECORDING SYSTEM

This application is the U.S. national phase of international application PCT/CH01/00407 filed 29 Jun. 2001 which designated the U.S., the entire content of which is hereby incorporated by reference.

FIELD OF THE INVENTION

The present invention relates to a device for recording the intraocular pressure over a period of time. More precisely, the invention relates to a device which can be placed on a contact lens on an eye to continuously monitor and record intraocular pressure over an extended period of time, e.g. 24 hours or more.

STATE OF THE ART

Glaucoma is a widespread disease (2–4% of a given population) characterized by an elevated intraocular pressure (IOP). This elevated IOP produces a gradual loss of peripheral vision.

There is therefore a need to have a detailed knowledge of IOP in glaucoma patients in order to provide reliable diagnostics or for setting up new therapies.

U.S. Pat. No. 5,179,953 discloses an intraocular pressure recording system made of scleral contact lens comprising a pressure transducer including one semiconductor strain gage which indents the sclera in a fixed position. This results in a fixed indentation connection of the gage to the sclera.

U.S. Pat. No. 4,089,329 discloses an intraocular pressure recording system made of a support, e.g. a ring, comprising a planar-faced pressure transducer which is adapted to crush (flatten) a portion of the scleral surface.

U.S. Pat. No. 4,922,913 discloses an intraocular pressure recording system made of a semi-rigid contact lens which contains a pressure transducer, e.g. a piezo-electric strain gage, which has a planar surface flattening a central portion of the cornea.

The publication entitled "Intraocular pressure measurement with instrumented contact lenses, Investigative Ophthalmology", April 1974, pp. 299–302, Vol. 13, No 4. discloses an intraocular pressure recording system made of a contact lens on which a strain gage is placed in a meridional angle of the corneosciera junction to measure angular changes. This pressure measurement relies on the theoretically predicted correlation between IOP and angular changes.

The publication entitled "A scieral buckle pressure gauge for continuous monitoring of intraocular pressure", Myron et al., International Ophthalmology 2, 3: 11–17 (19890), discloses an implantable variable resistance pressure gage made of a strip which has to be placed and attached around the periphery of the sclera by a surgeon.

The publication entitled "Distensibility measurements of the rabbit eye", Tittel & Richards, Investigative Ophthalmology, 1971, vol. 10, No 10, 800–809, discloses the use of a circumference gage of the same type of the scleral buckle pressure gauge which was implanted on rabbits.

The currently used devices are either too aggressive for the patient or not accurate enough or do necessitate to topically anesthetize the patient's eye and/or to surgically operate prior to testing.

Thus there is presently a need for a comfortable and accurate testing which simultaneously does not require a physician.

The present invention is directed to meeting the above cited needs. It concerns an intraocular pressure recording system comprising a soft contact lens and an active strain gage fixed to said contact lens, characterized by the fact that said active strain gage has a circular arc shape and is situated around the center of said soft contact lens. This particular configuration allows one to measure very precisely spherical deformations of the eyeball which are correlated to IOP.

Using the object of the present invention allows a more accurate measurement of the eyeball and i.e. the IOP. Furthermore, due to the fact that the strain gage is not in direct contact with the eye, the patient feels very comfortable and his vision remains almost completely unimpaired. In fact he has a similar feeling as a person wearing usual contact lenses.

In a preferred embodiment, the active strain gage is made of a resistive metal, the gage resistance varying according to the gage strain.

Preferably the active strain gage is a continuous longitudinal element, e.g. a wire or a microfabricated object (MEMS) which result in a foil strain gage on which a metallic layer is deposited or laminated on a substrate (e.g. polyimide) and patterned by wet or dry etch in a desired configuration (grid).

The wire diameter may be comprised between 0.01 mm and 0.1 mm.

MEMS gages are manufactured according to Integrated Circuit manufacturing processes, this technique offers the following advantages: Every single parameter of the strain gage can be controlled very precisely (e.g. thickness of the metallic strain gage layer) as well as the design of the grid that can be realized with a precision of about 1 µm and gives the possibility to build really specific gages. Moreover the process is completely and easily reproducible.

As material which can be used for the gages of the present invention we can cite Polyimide as substrate and platinum as metallic layer, but any kind of resistive material as well as semiconductor or resistive polymer could be used. Polyimide as substrate is really suitable because it is well known and used in MEMS technology and it is biocompatible as well as platinum which has also a good strain gage factor.

For a variable resistance pressure gage, in order to have a more accurate measurement, the gage resistance has to be maximized and its grid area has to cover all the zones which have to be monitored. In the present invention, this can be achieved by folding the longitudinal element into several portions which are arranged parallel to each other.

In one preferred embodiment the active gage forms almost a complete circle.

Several active gages can be placed on the contact lens. They can consist of several circular arc portions placed along the same circumference or they consist of several concentric circles.

In another embodiment, the intraocular pressure recording system furthermore comprises passive strain gages for thermal compensation which have preferably a general circular arc shape made of a continuous meridional element placed in such a way that several of its portions are radially arranged, i.e. their direction cross the lens center C. Such a configuration results in a more accurate measurement.

In another preferred embodiment, the intraocular pressure recording system comprise four gages in a Wheatstone Bridge configuration, e.g. two active gages and two passives ones being placed alternatively on the bridge.

The active gage(s) can be placed at any distance from the center of the contact lens. In a preferred embodiment, the active gage is shaped in order to be placed on the corneoscleral junction which represents a zone where changes in IOP induce maximum corneal deformation.

The gage(s) can be fixed to the lens by any method. It/They can be first fixed to a substrate which is then fixed on the lens or it/they can be directly fixed to the lens.

The data transmission with the gage(s) can be achieved in using a wire transmission or (preferably) a wireless transmission system.

In addition to the gage(s) the contact lens can also comprise other measuring devices such as an ElectroRetinoGraph or a chemical analysis sensor.

The present invention will be more fully appreciated from the following detailed examples taken together with the drawings in which.

Figure 1:
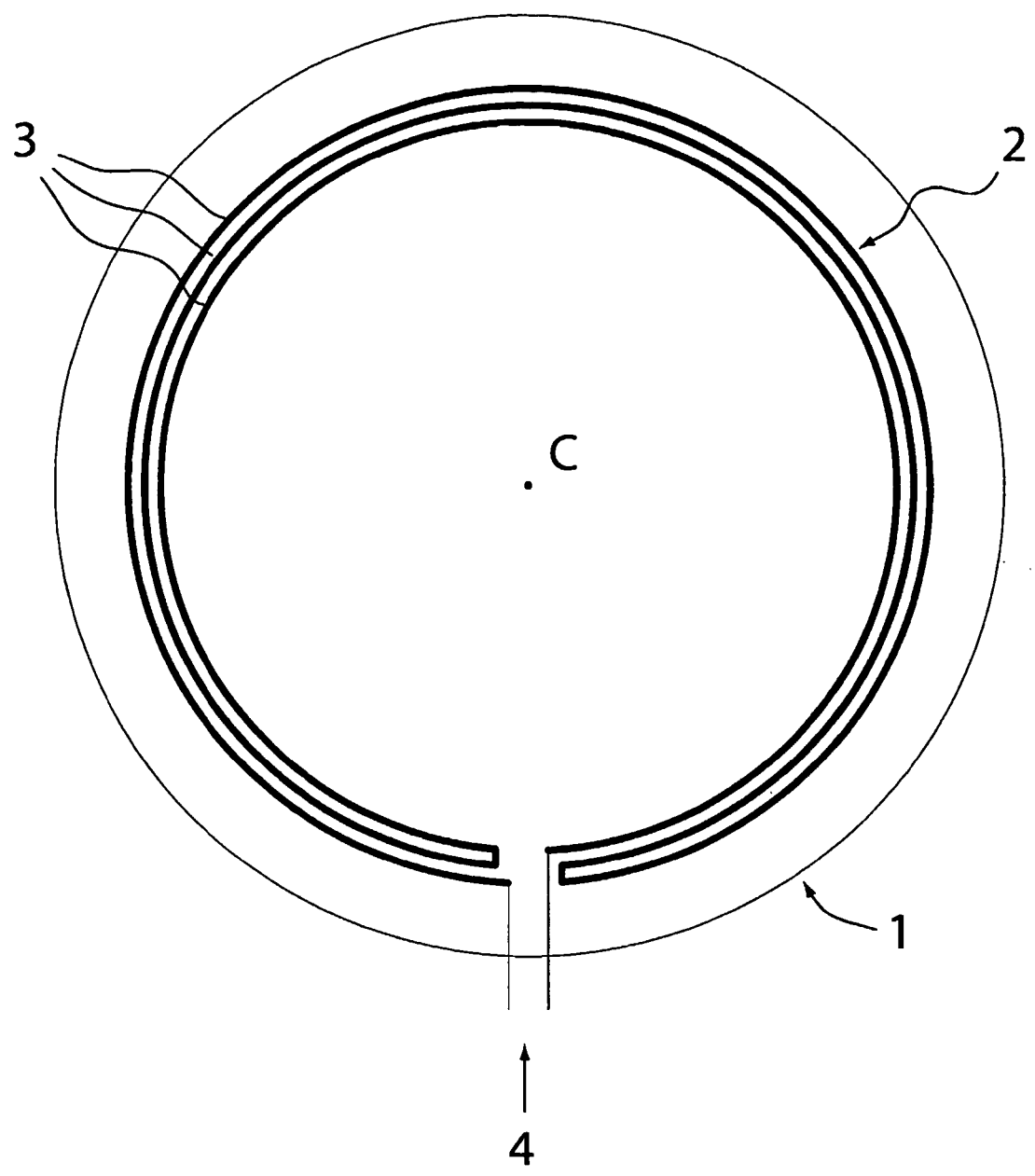
FIG. 1 shows a first intraocular pressure recording system according to the invention.
Figure 2:
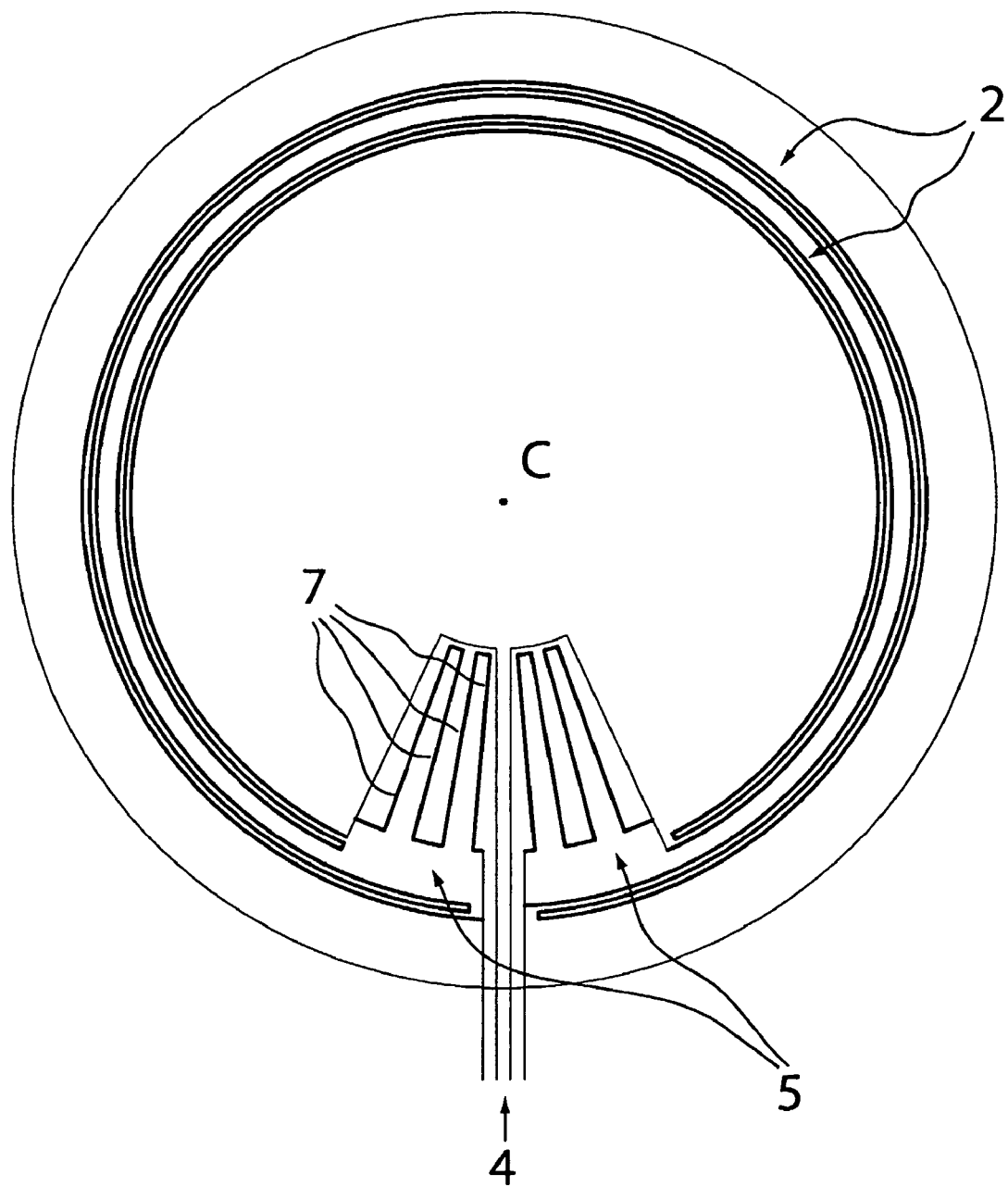
FIG. 2 shows a second intraocular pressure recording system according to the invention.
Figure 3:
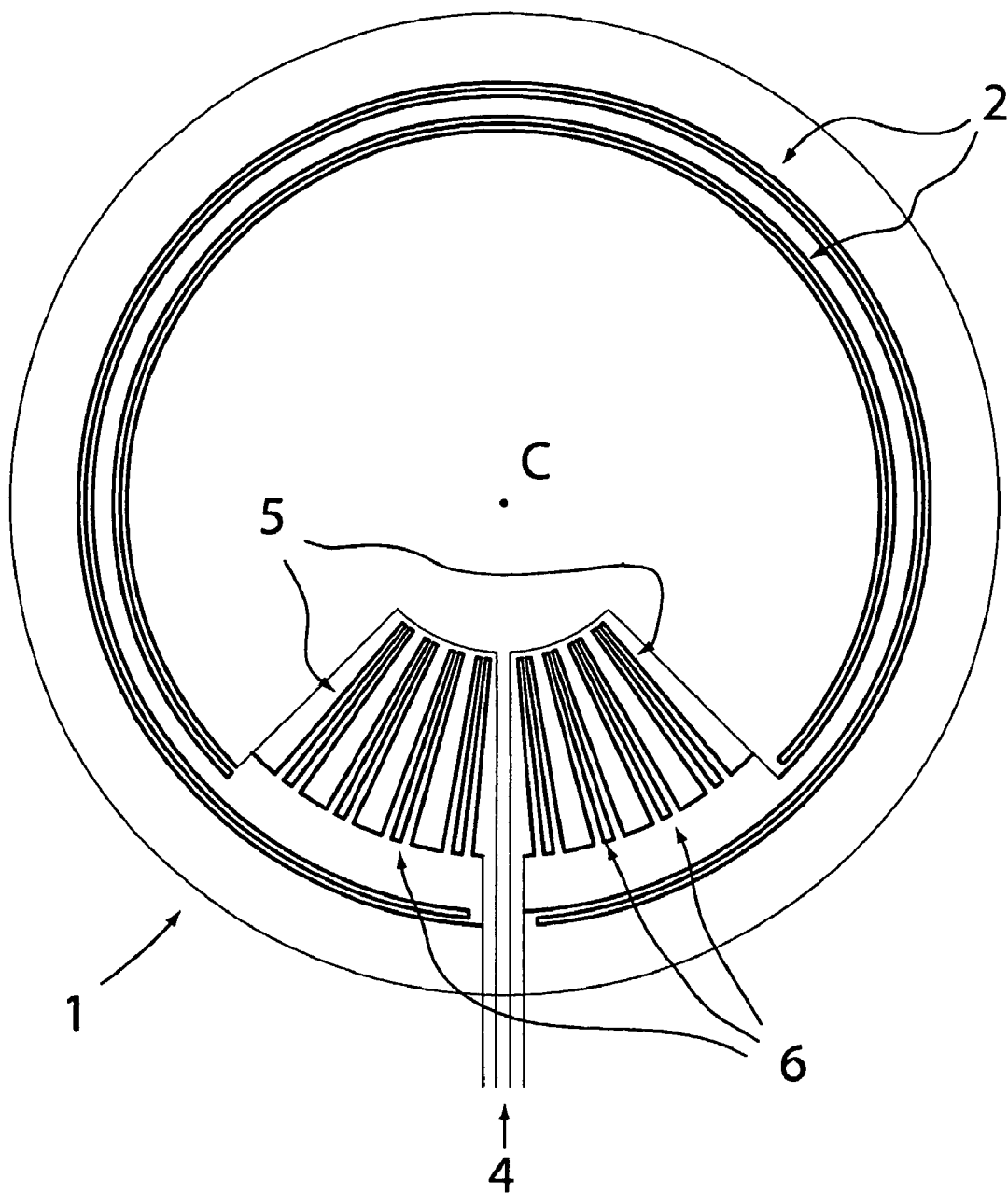
FIG. 3 shows a third intraocular pressure recording system according to the invention.

As shown in FIG. 1 to 3, the intraocular pressure recording system comprises a soft contact lens 1 including a circular active strain gage 2 disposed around the lens center C. Active strain gage 2 is made of a continuous longitudinal wire which is folded in such a way that several of its portions 3 are parallel to each other and therefore concentric. Both ends 4 of the wire are connected to a data transmission system (not illustrated). The transmission may be achieved via a wireless telemetry system.

FIGS. 2 and 3 illustrate another preferred device similar to the one of FIG. 1 but comprising four gages in a Wheatstone Bridge configuration, e.g. two active gages and two passive ones being placed alternatively on the bridge. The passive strain gages 5 are made of a continuous wire folded into several portions 7 which are radially arranged, i.e. their direction cross the lens center C. The wire portions of active and passive gages can be very close to minimize the gage area or more spaced to maximize thermal exchanges and gage area. FIG. 3 shows a configuration with a quite big passive gage area with wire portions grouped into more blocks 6. With such configurations (FIGS. 2 and 3), the two active strain gages 2 measure one type of strain (the strongest one) and double the sensitivity of the measure on the Wheatstone Bridge. The two passive strain gages 5 measure another type of strain (the weakest one) and compensate for thermal derivation, active and passive gages having the same resistance value without any stress applied.

Figure 4:
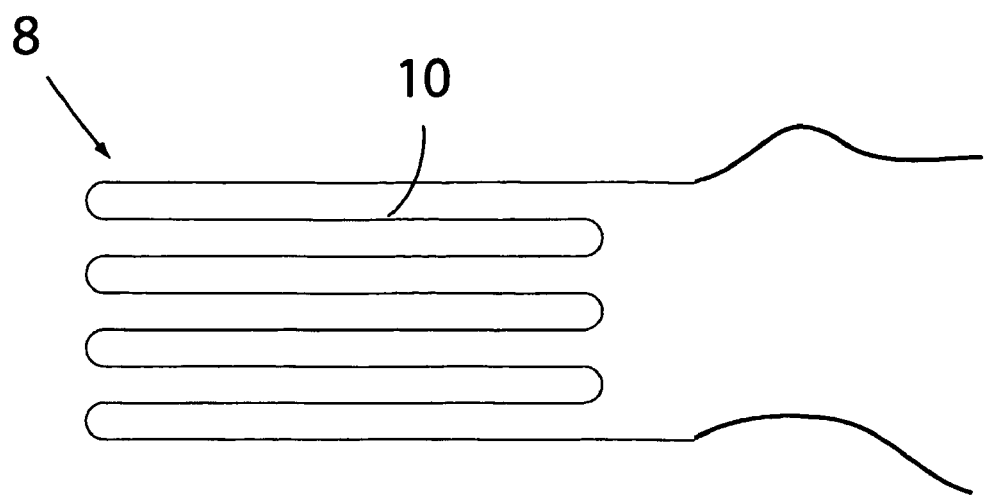
FIG. 4 shows a strain gage which can be used with the present invention.
Figure 5:
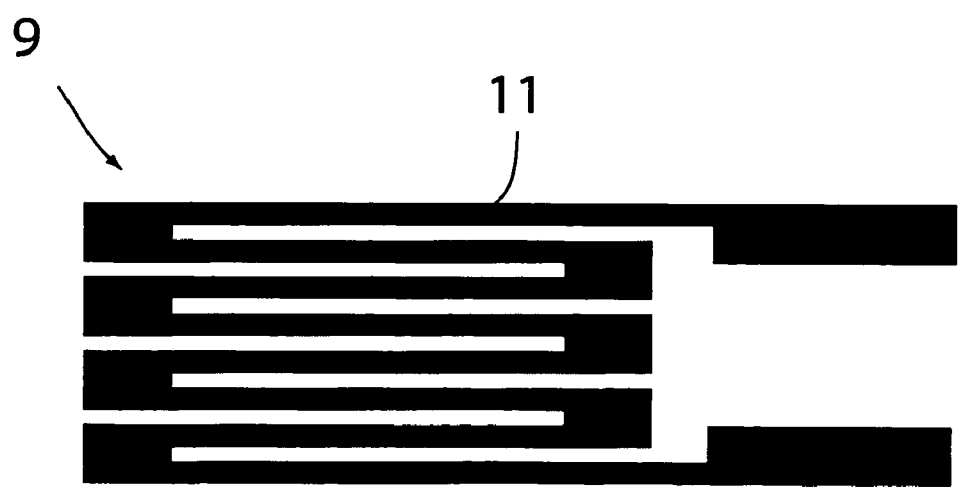
FIG. 5 shows another strain gage which can be used with the present invention.

FIG. 4 illustrates a strain gage 8 which is made of a wire 10 and FIG. 5 illustrates another strain gage 9 (MEMS) with its grid 11 which is made according to a micromachining process.

Figure 6:
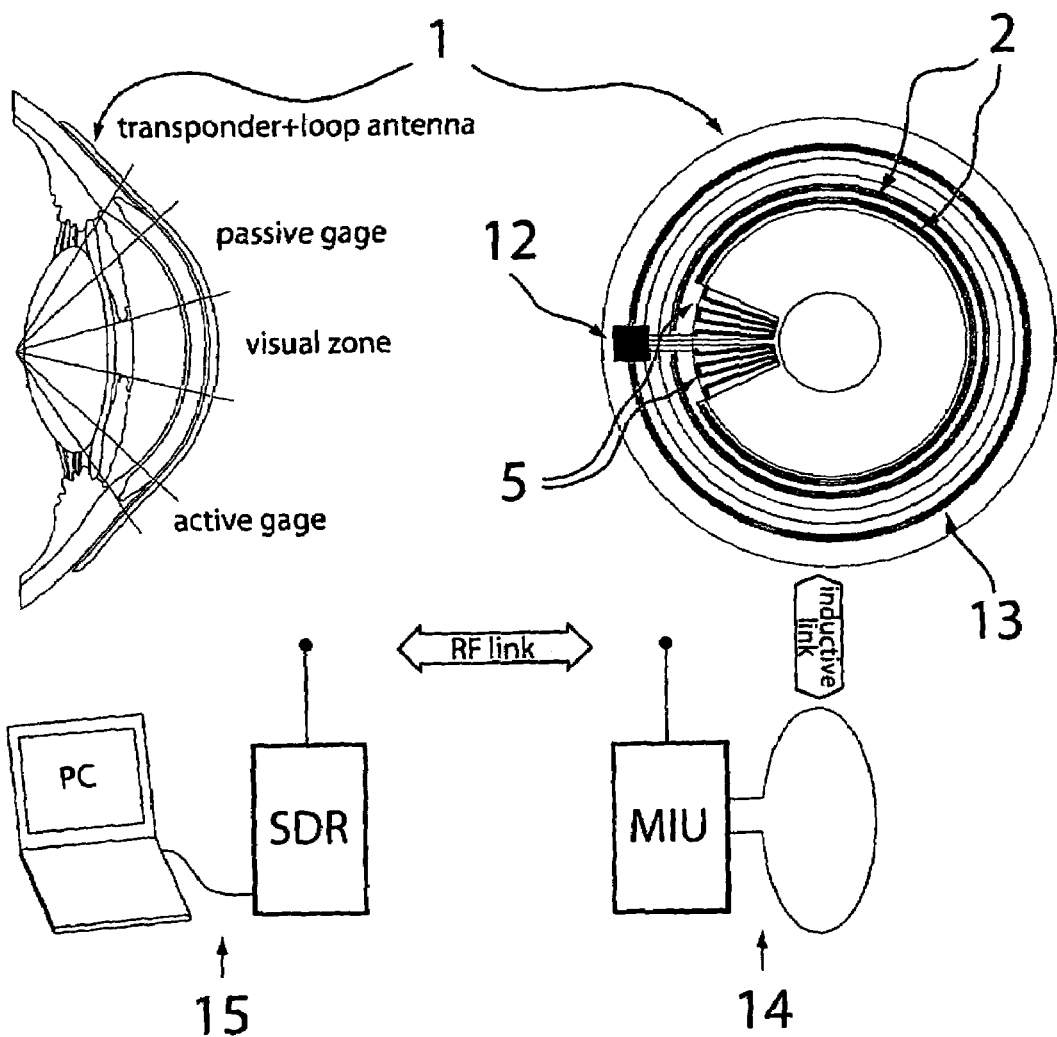
FIG. 6 shows a simplified block diagram of an intraocular pressure recording system according to the invention with a telemetry system embedded and extracorporal receiving units.

FIG. 6 shows the simplified block diagram of a preferred configuration of the entire system with a telemetry system embedded and extracorporal receiving units. The contact lens comprise the sensor, it is to say active 2 and passive 5 gages on a Wheatstone Bridge configuration, a low-power transponder 12 and a loop antenna 13. Powering and communication are performed contactlessly between the transponder and an extracorporal mobile interrogation unit (MIU) 14 via coupled loop antennas. The MIU provides the sensor with energy and passes the received transponder data to the stationary data receiver (SDR) 15 via a second RF link. The SDR completes the monitoring setup. It stores and displays the received data.

The invention claimed is:

1. Intraocular pressure recording system comprising a soft contact lens having a center and an active strain gage fixed to said contact lens, wherein said active strain gage is placed at a distance from the center of the contact lens, is not in direct contact with an eye, and comprises a portion having a circular arc shape which is situated around the center of said soft contact lens.

2. Intraocular pressure recording system according to claim 1 wherein said active strain gage is made of a resistive material.

3. Intraocular pressure recording system according to claim 2 wherein said active strain gage is a continuous longitudinal element.

4. Intraocular pressure recording system according to claim 3 wherein said continuous longitudinal element comprises portions and is placed in such a way that several of said portions are disposed parallel to each other.

5. Intraocular pressure recording system according to claim 3 wherein said continuous longitudinal element is microfabricated.

6. Intraocular pressure recording system according to claim 3 wherein said continuous longitudinal element is a wire.

7. Intraocular pressure recording system according to claim 1 further comprising a passive strain gage.

8. Intraocular pressure recording system according to claim 7 wherein said passive strain gage has a general circular arc shape made of a continuous meridional element comprising portions and is placed in such a way that several of said portions are radially arranged.

9. Intraocular pressure recording system according to claim 8 wherein said continuous meridional element is microfabricated.

10. Intraocular pressure recording system according to claim 8 wherein said continuous meridional element is a wire.

11. Intraocular pressure recording system according to claim 7 including a wireless telemetry system for data transmission with said passive strain gage.

12. Intraocular pressure recording system according to claim 7 including a wireless telemetry system for data transmission with said active and passive strain gages.

13. Intraocular pressure recording system according to claim 1 wherein said active strain gage is shaped in order to be placed on the corneosclera junction.

14. Intraocular pressure recording system according to claim 1 including a wireless telemetry system for data transmission with said active strain gage.

15. Intraocular pressure recording system according to claim 1 wherein said contact lens further comprises other measuring devices.

16. Intraocular pressure recording system according to claim 1 wherein the system comprises several active gages.

17. Intraocular pressure recording system according to claim 1 wherein the system comprises several passive gages.

18. Intraocular pressure recording system according to claim 1 wherein the system comprises gages in a Wheatstone bridge configuration.

19. Intraocular pressure recording system according to claim 18 wherein the Wheatstone bridge configuration comprises two active gages and two passive gages placed alternatively on the bridge.

20. Intraocular pressure recording system according to claim 1 wherein said contact lens further comprises an ElectroRetinoGraph or a chemical analysis sensor.

21. Intraocular pressure recording system according to claim 1 wherein said contact lens is a silicone contact lens.

22. Intraocular pressure recording system comprising:
a soft contact lens having a center,
an active strain gage fixed to said contact lens, wherein said active strain gage is placed at a distance from the center of the contact lens, is not in direct contact with an eye, and comprises a portion having a circular arc shape which is situated around the center of said soft contact lens, and
a passive strain gage, wherein said passive strain gage has a general circular arc shape made of a continuous meridional element comprising portions and is placed in such a way that several of said portions are radially arranged.

23. Intraocular pressure recording system comprising:
a soft contact lens having a center, and
an active strain gage fixed to said contact lens, wherein said active strain gage is placed at a distance from the center of the contact lens, is not in direct contact with an eye, and comprises a portion having a circular arc shape which is situated around the center of said soft contact lens, and
wherein the system comprises gages in a Wheatstone bridge configuration.

* * * * *